United States Patent [19]

Naito et al.

[11] Patent Number: 4,610,490
[45] Date of Patent: Sep. 9, 1986

[54] DOOR-OPERATING APPARATUS FOR ANALYZER

[75] Inventors: Mitsuo Naito; Toshio Watanabe, both of Tokyo, Japan

[73] Assignee: Seiko Instruments & Electronics Ltd., Tokyo, Japan

[21] Appl. No.: 637,109

[22] Filed: Aug. 2, 1984

[30] Foreign Application Priority Data

Aug. 18, 1983 [JP]  Japan .................. 58-127572[U]

[51] Int. Cl.⁴ .................................. A47B 81/00
[52] U.S. Cl. ........................ 312/272; 312/273; 312/309
[58] Field of Search ............ 49/66, 69, 73; 312/273, 312/309, 271, 272, 274; 220/255

[56] References Cited

U.S. PATENT DOCUMENTS 678,235  7/1901  Ferracioli ..................... 312/272
2,814,544  11/1957  Cornish ....................... 312/271

FOREIGN PATENT DOCUMENTS 866594  9/1956  United Kingdom ............ 312/274
855460  11/1960  United Kingdom ............ 312/274

Primary Examiner—William E. Lyddane
Assistant Examiner—Gerald A. Anderson
Attorney, Agent, or Firm—Robert E. Burns; Emmanuel J. Lobato; Bruce L. Adams

[57] ABSTRACT

A door-operating apparatus for an analyzer, comprising first and second rails provided on an analyzer body, a movable member provided on said first rail, a slider fixed to said movable member, a sample table and an angle piece provided on said slider, a window frame provided movably on said second rail, a holding member attached to said window frame, and a pivotable link of which ends are supported on said holding member and said angle piece respectively, said slider being moved along said first rail so that said sample table is controlled from the outside.

4 Claims, 3 Drawing Figures

DOOR-OPERATING APPARATUS FOR ANALYZER

BACKGROUND OF THE INVENTION

The device of this application relates to a door-operating apparatus for an X-ray analyzer, and more particularly to a door-operating apparatus for an X-ray analyzer which can move a drawer on which a sample table is placed out of an analyzer body in synchronism with the opening of the door.

It is fairly difficult to set or reset a sample on a sample table provided within a conventional sealed apparatus. In order to make this operation easier, proposals have been made to increase the size of the door of the apparatus to widen its opening, or position the sample table closer to the door, but the construction of the apparatus makes these remedies difficult.

An object of the device of this application is to provide an extremely effective means of eliminating this defect. The device of this application is constructed so that, during the operation of opening the door of the apparatus to which the device is applied, a slider on which a sample table is placed is moved out of the apparatus in synchronism with the opening of the door, and the slider supporting the sample table is moved inward in synchronism with the closing of the door so that it is set at a measurement position within the apparatus.

BRIEF DESCRIPTION OF THE DRAWINGS

The accompanying drawings show an embodiment of the device of this application, wherein.

Figure 1:
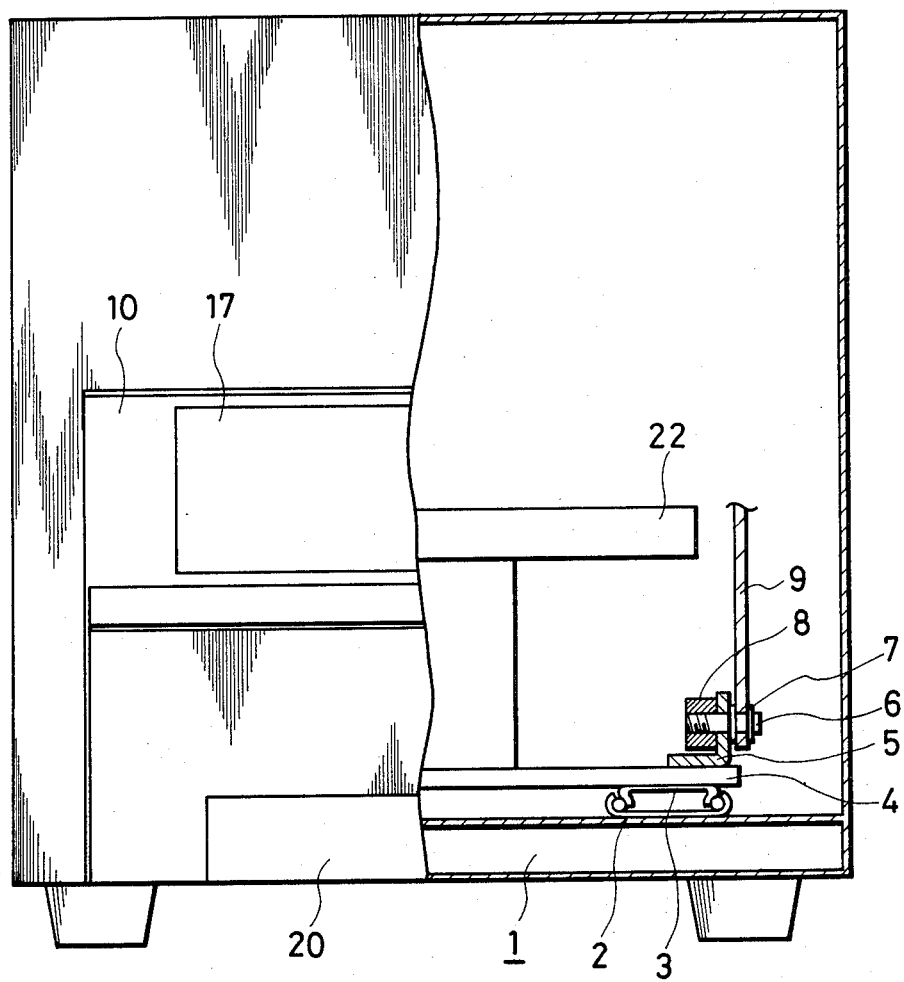
FIG. 1 is a front elevation thereof.

Parts of the apparatus are identified as follows:
1 . . . analyzer body, 2 . . . rail, 3 . . . movable member, 4 . . . slider, 5 . . . angle piece, 5a . . . elongated hole, 6 . . . shaft, 7 . . . stop ring, 8 . . . nut, 9 . . . link, 10 . . . window frame, 11 . . . holding member, 12 . . . shaft, 13 . . . stop ring, 14 . . . guide roller, 15 . . . rail, 16 . . . screw, 17 . . . lead glass, 18 . . . holding plate, 19 . . . screw, 20 . . . handle, 21 . . . screw, 22 . . . sample table.

The device of this application will now be described in detail, with reference to the accompanying drawings. In the drawings, reference numeral 1 denotes an analyzer body, 2 denotes a rail fixed to the analyzer body 1, 3 denotes a member provided on the rail 2 so that the member 3 can move along the rail 2, 4 denotes a slider fixed to the movable member 3, 5 denotes an angle piece provided with an elongated hole 5a and fixed to the slider 4, 6 a shaft engaged in the elongated hole 5a in the angle piece 5 which can be moved to and fixed to a suitable position in the hole 5a, 7 denotes a stop ring fitted around the shaft 6, 8 denotes a nut holding the shaft 6 to the angle piece 5, 9 denotes a pivotable link supported at one end on the shaft 6, 10 denotes a window frame, 11 denotes a holding member fixed to the window frame, 12 denotes a shaft on which the other end of the link 9 is supported, 13 denotes a stop ring holding the shaft 12 to the holding member 11, 14 denotes a guide roller fixed to the window frame 10, 15 denotes a rail guiding the guide roller 14, 16 denotes a screw holding the rail 15 to the analyzer body 1, 17 denotes lead glass set in the window frame 10, 18 denotes a holding plate fixing the lead glass 17, 19 denotes a screw fixing the holding plate 18 to the window glass 10, 20 denotes a handle attached to the slider 4, 21 denotes a screw fixing the handle 20 to the slider 4, and 22 denotes a sample table attached to the slider 4.

Figure 2:
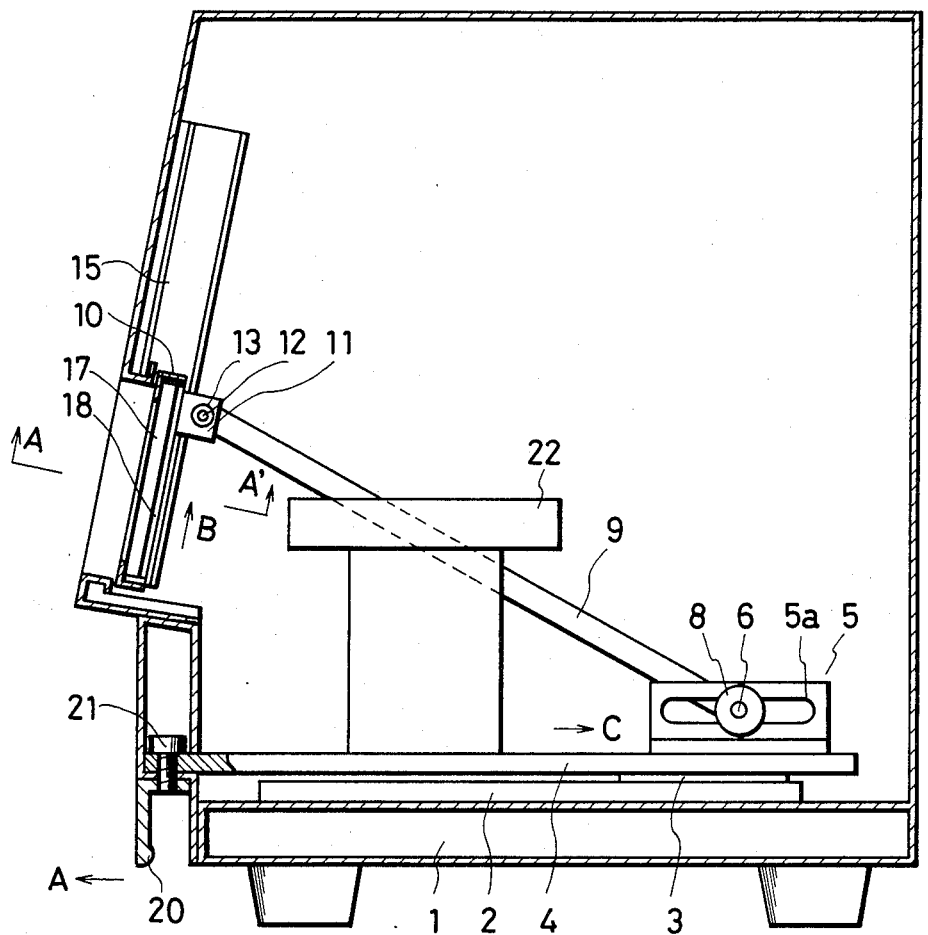
FIG. 2 is a sectioned side elevation thereof.
Figure 3:
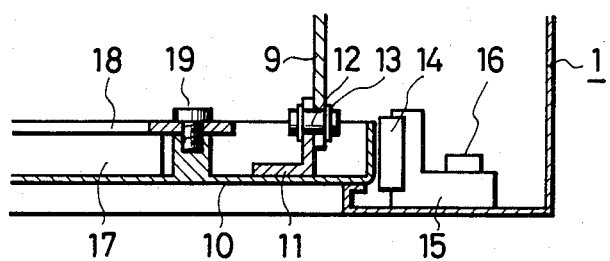
FIG. 3 is a horizontal section taken along the line 3—3 of FIG. 2.

The operation of this device will now be described. Referring to FIG. 2, when the handle 20 is pulled manually in the direction of the arrow A, the slider 4 moves together with the movable member 3, guided by the rail 2, and the sample table 22 moves therewith in the same direction. During this time, the link 9 of which one end is engaged with the angle piece 5 by the shaft 6 is pivoted about the other end thereof connected to the holding member 11 which is fixed to the window frame 10. Accordingly, the window frame 10 is moved in the direction of the arrow B, i.e. in a substantially vertical direction, so that the front of the analyzer body 1 is opened. Conversely, when the slider 4 slides in the direction of the arrow C, all the parts that move when the handle 20 is pulled in direction A move in the opposite direction. Consequently, the window frame 10 returns to the position shown in FIG. 2 to close the analyzer body 1 with the sample table 22 housed therein. The window frame 10 moves guided by the guide roller 14 and rail 15.

The analyzer is also provided with a microswitch (not shown), which outputs an "OK" signal to a controller (not shown) when the analyzer is in the sealed state shown in FIG. 2 to authorize the start of measurement, and a safety lock (not shown) locking the analyzer in this sealed state.

As described above, this device can provide a door unit which can be moved in synchronism with the pulling out of a slider, in which a door (window frame) can be moved by actuating a slider on which a sample table is placed. This device ensures that samples can be set and reset therein simply, and is very effective.

We claim:

1. An analyzer comprising an analyzer body having a bottom and a front wall having a lower opening near the bottom and an upper opening spaced from the bottom,
   a first rail on said bottom extending forwardly and rearwardly of the analyzer bottom,
   a slider slidable on said rail between a rearward position in which said slider is in said analyzer body and a forward position in which said slider extends out through said lower opening in said front wall,
   means on said slider for moving it between said rearward position and said forward position,
   a sample table mounted on said slider,
   a second rail along side said upper opening in said front wall and a window guided by said second rail for movement between a lower position in which said window closes said upper opening and an upper position in which said window is above said upper opening so as to leave said upper opening open, and
   a link having a lower end pivotally connected to said slider and an upper end pivotally connected to said window for operably connecting said window with said slider for movement of said window from said lower position to said upper position upon movement of said slider from said rearward position to said forward position,
   said sample table being of a height to be accessible through said open upper opening when said slider is in said forward position.

2. A analyzer according to claim 1, in which an elongate angle piece is fixed on said slider, said angle piece having a vertical portion in which there is an elongate horizontal slot, the pivotal connection of said lower end of said link with said slider comprising a shaft extending through said slot and a hole in said lower end of said link and a nut for holding said shaft to said angle piece.

3. An analyzer according to claim 1, in which said window comprises a window frame, a window glass set in said frame and guide rollers fixed to said window frame and guided by said second rail in movement of said window between said lower position and said upper position.

4. An analyzer according to claim 1, in which said window further comprises an angular holding member fixed to said window frame, the pivotal connection of said upper end of said link with said window comprising a shaft extending through aligned holes in said holding member and said upper end of said link.

* * * * *